(12) United States Patent  
Wright

(10) Patent No.: US 7,168,095 B2
(45) Date of Patent: Jan. 30, 2007

(54) FACE PROTECTOR AND METHOD OF USE

(76) Inventor: Jerry D. Wright, 17450 Greenridge Rd., Middletown, CA (US) 95461

( * ) Notice: Subject to any disclaimer, the term of this patent is extended or adjusted under 35 U.S.C. 154(b) by 13 days.

(21) Appl. No.: 11/083,573

(22) Filed: Mar. 18, 2005

(65) Prior Publication Data

US 2005/0204446 A1 Sep. 22, 2005

Related U.S. Application Data

(60) Provisional application No. 60/606,948, filed on Sep. 3, 2004, provisional application No. 60/554,321, filed on Mar. 18, 2004, provisional application No. 60/554,320, filed on Mar. 18, 2004.

(51) Int. Cl.
*A41B 1/00* (2006.01)
*A61F 9/02* (2006.01)

(52) U.S. Cl. ............................ 2/9; 2/423; 2/425; 2/427; 2/430

(58) Field of Classification Search .................... 2/425, 2/427, 428, 429, 430, 206, 423, 424, 9
See application file for complete search history.

(56) References Cited

U.S. PATENT DOCUMENTS

| 797,293 | A | * | 8/1905 | Lang et al. ....................... 2/12 |
| 2,827,900 | A | * | 3/1958 | Marietta ................ 128/206.28 |
| 2,903,700 | A | * | 9/1959 | Finken et al. ...................... 2/10 |
| 5,093,938 | A | * | 3/1992 | Kamata .......................... 2/424 |
| 5,138,723 | A | * | 8/1992 | Bolle ............................. 2/430 |
| 5,617,588 | A | * | 4/1997 | Canavan et al. ................ 2/428 |
| 5,911,308 | A | * | 6/1999 | Chafitz et al. ..................... 2/9 |
| 6,381,749 | B1 | * | 5/2002 | Cyr .................................. 2/9 |
| 6,886,183 | B2 | * | 5/2005 | DeHaan et al. ................. 2/6.7 |
| 6,966,067 | B1 | * | 11/2005 | Lusk ................................. 2/9 |
| 2004/0025229 | A1 | * | 2/2004 | Takahashi et al. ............. 2/412 |
| 2005/0036100 | A1 | * | 2/2005 | Rice et al. ..................... 351/62 |
| 2005/0278833 | A1 | * | 12/2005 | Pierce ........................... 2/424 |
| 2006/0090234 | A1 | * | 5/2006 | Cyr .................................. 2/9 |

* cited by examiner

*Primary Examiner*—Rodney M. Lindsey
(74) *Attorney, Agent, or Firm*—Stephen C. Beuerle; Procopio Cory Hargreaves & Savitch LLP

(57) ABSTRACT

A method of using a face protector includes providing a face protector including a lens and a face plate configured to protect the forehead, eyes, cheeks, jaw, chin, mouth, ears, and nose of a user without protecting substantially the remainder of the user's head; applying the face protector to the user's head; wearing the face protector during an activity; and removing the face protector after the activity.

18 Claims, 10 Drawing Sheets

FACE PROTECTOR AND METHOD OF USE

CROSS-REFERENCE TO RELATED APPLICATIONS

This application claims the benefit under 35 U.S.C. 119(e) of the following provisional patent applications: U.S. Provisional Application 60/554,320, filed Mar. 18, 2004; U.S. Provisional Application 60/554,321, filed Mar. 18, 2004; and U.S. Provisional Application 60/606,948, filed Sep. 3, 2004.

FIELD OF THE INVENTION

The present invention relates, in general, to devices and methods for protection of a wearer's face from outdoor environmental elements (e.g., cold, rain, wind, debris, hail, snow).

BACKGROUND OF THE INVENTION

Current products on the market including, but not limited to, motorcycle helmets, snowboarding helmets, ski helmets, etc., all are meant to protect the entire head from falls or injury to the entire head and not used solely for front head and face protection. All are comprised of some type of hard material, are full-shelled helmets, are not compactable, and do not allow for efficient stowing, storage. These helmets are also heavy and are susceptible to mildew when used in wet environments and not dried or stored in dry environments (e.g., boats).

SUMMARY OF THE INVENTION

To solve these problems and others, the present invention involves a face protector to protect the front of a user's head (i.e., forehead, face, eyes, cheeks, jaw, chin, mouth and nose) from the elements associated with outdoor activities (or other activities) such as, but not limited to, during boat travel in sport leisure and commercial fishing, snowboarding, skiing, snowmobiling, hiking, hunting, paint ball, law enforcement, fire fighting, motorcycling, dune buggy or rails, ATV, air soft, spectator sports (e.g., NASCAR car racing, NFL/college football, NHL/college hockey), commercial activities such as airline industry, landscaping, and governmental activities such as military, lake patrols, etc.

In an aspect of the invention, the face protector includes a face plate and a removable/interchangeable lens that together cover the forehead, eyes, face, cheeks, jaw, chin, mouth, ears, and nose. The face protector extends from the top of the forehead down to the just behind the ear portion and covers the front of the face. The removable/interchangeable lens may come in clear, smoked, yellow, and tinted versions to protect the eyes while allowing vision. A stretchable, elastic, water-resistant strap, which connects to the face plate at the ear portion with a strap clip, is used to hold the face protector in position in front of the user's face. The face protector is small, light-weight, stowable, comfortable, compactable, durable, and water-resistant.

In another aspect of the invention, the face protector includes a face plate similar to that mentioned above pivotally connected to a stationary goggle frame. The frame is connected to the user's head with a stretchable, elastic, water-resistant strap. This allows the face plate to be pivoted upward and rearward, retracted to a position where the face plate is no longer in front of the user's face. When the user desires face protection, the face plate can be pivoted downward, to a deployed position in front of the user's face.

Implementations of either or both of the face protectors described above may include one or more of the following: a face cushion, an insert between the face cushion and the face plate, the insert includes ventilation paths for providing ventilation to the inside of the face protector, a replaceable forehead logo insert, opposite headphone speakers in ear portions with a wire/plug (for plugging into a separate CD player, MP3 player, Apple IPOD (or other musical device with hard drive), AM and/or FM receiver/tuner, or two-way radio), an AM and/or FM receiver/tuner, a flashlight in the forehead portion, and a two-way radio in the face plate with an attached microphone in mouth portion.

A further aspect of the invention involves a method of using a face protector. The method includes providing a face protector including a lens and a face plate configured to protect the forehead, eyes, cheeks, jaw, chin, mouth, ears, and nose of a user without protecting substantially the remainder of the user's head; applying the face protector to the user's head; wearing the face protector during an activity; and removing the face protector after the activity.

Implementations of the aspect of the invention described immediately above may include one or more of the following: the face protector further includes a strap, and applying includes applying the face protector to the user's head by sliding the face plate and strap over the users head and securing the face plate in position in front of the user's face with the strap; providing includes providing the face protector with a goggle-shaped cushion member and a goggle-shaped insert disposed between the goggle-shaped cushion member and the face plate; and the goggled-shaped insert includes means for ventilating the face protector.

DETAILED DESCRIPTION OF PREFERRED EMBODIMENTS

Figure 1:
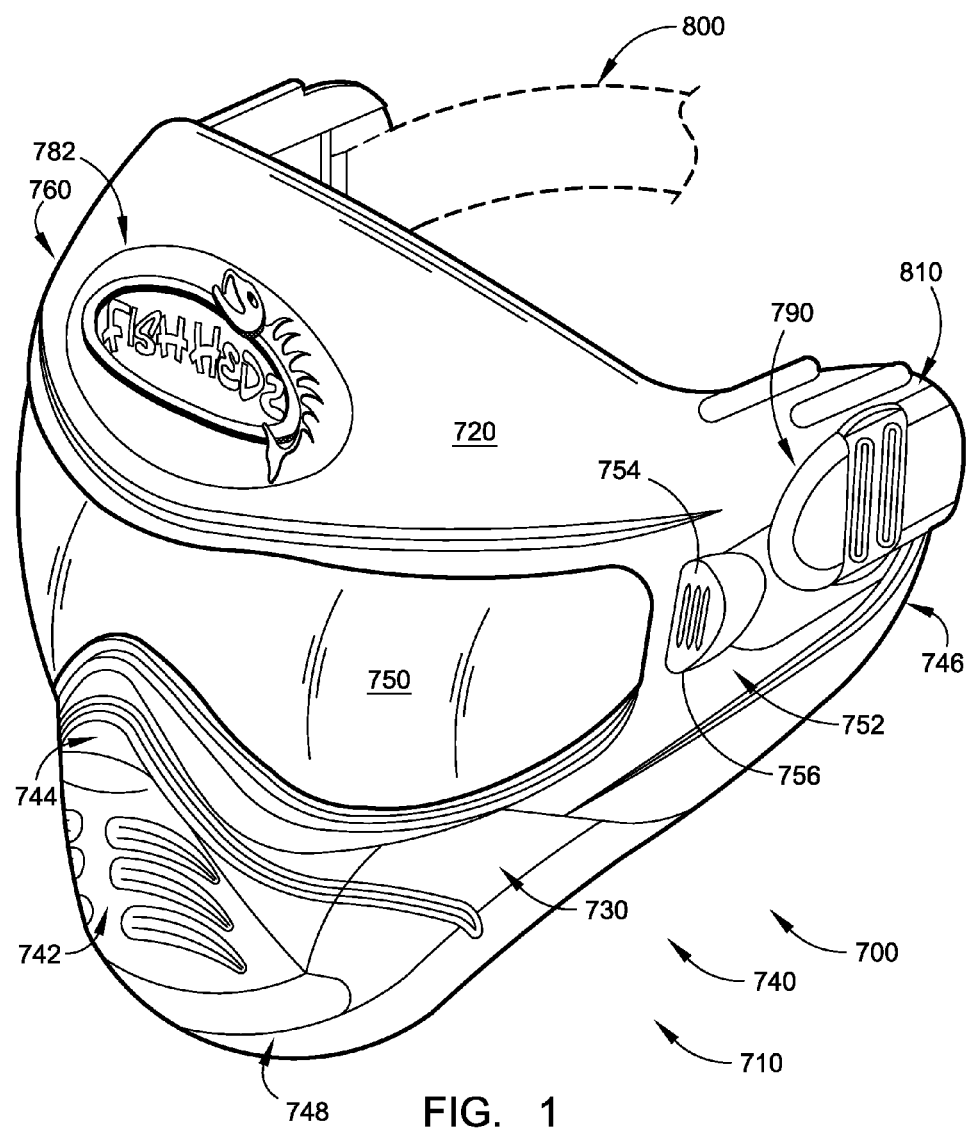
FIG. 1 is a front perspective view of an embodiment of a face protector.
Figure 4:
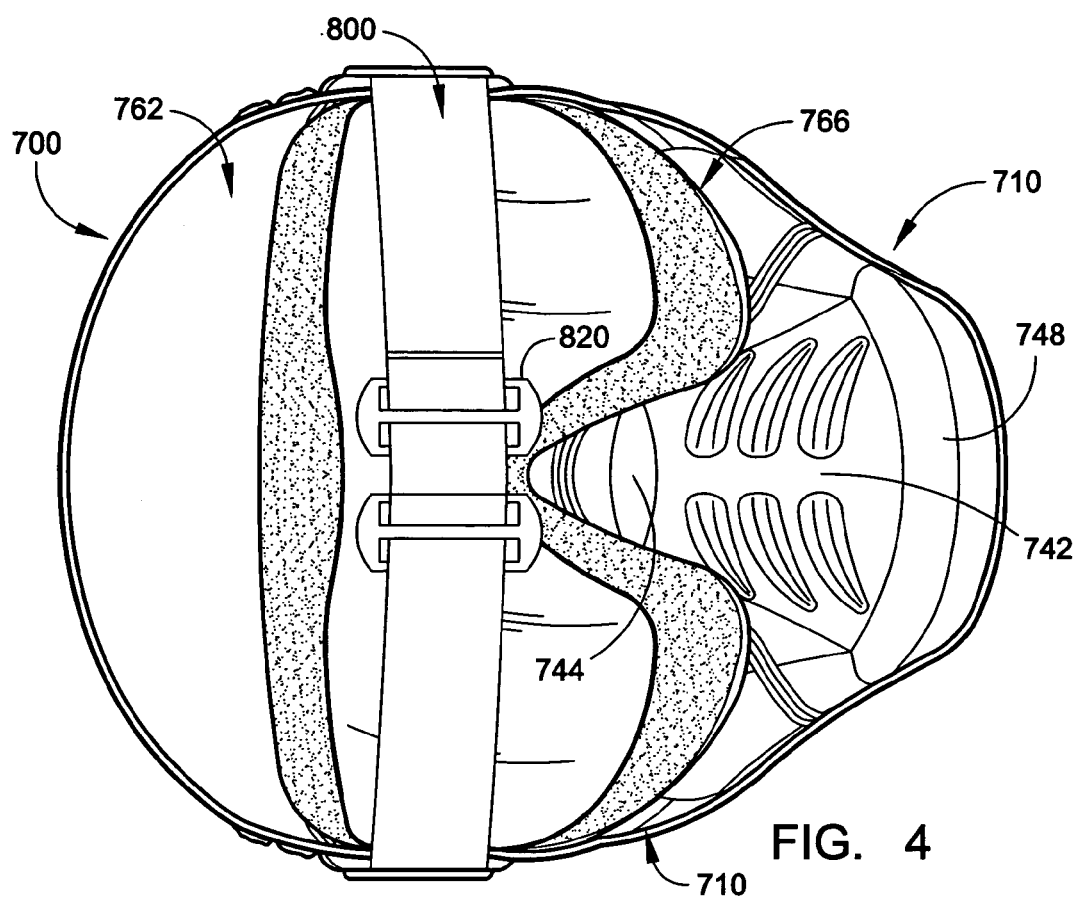
FIG. 4 is a rear elevational view of the face protector illustrated in FIG. 1.
Figure 2:
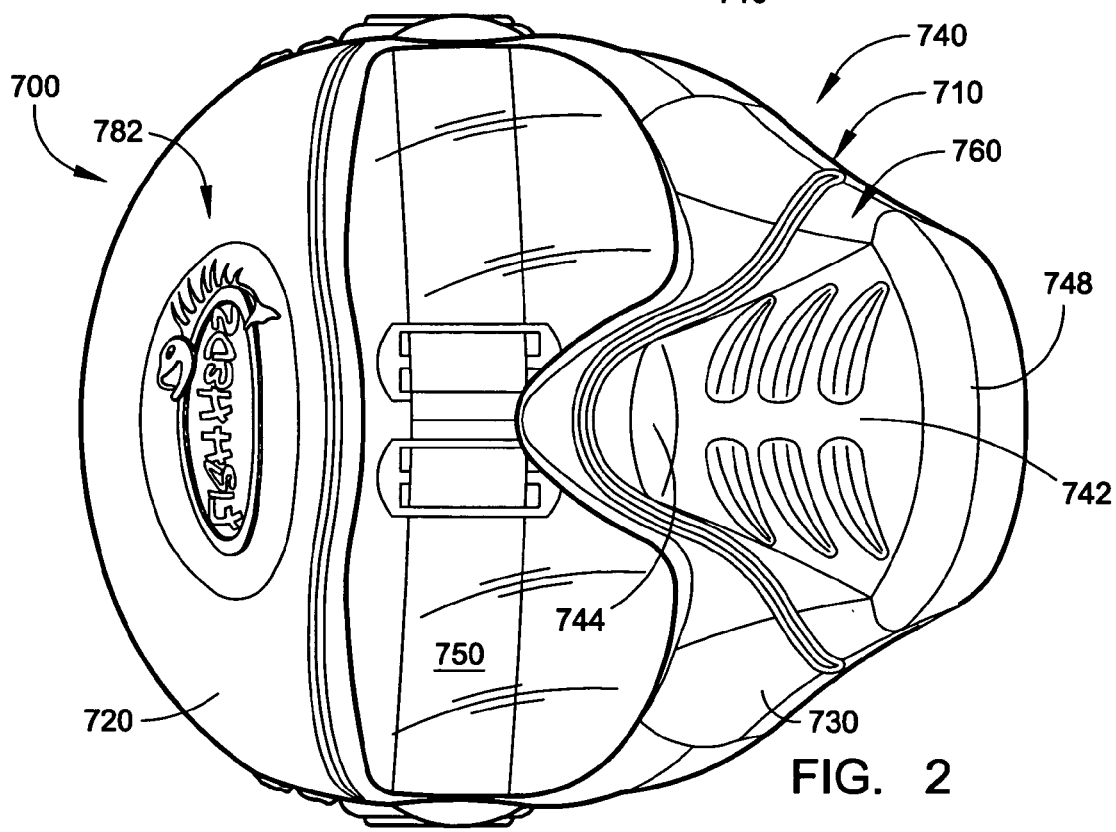
FIG. 2 is a front elevational view of the face protector illustrated in FIG. 1.

With reference to FIGS. 1–10, an embodiment of a face protector 700 and method of using the same will be described. The face protector 700 protects the front of a user's head (i.e., forehead, face, eyes, cheeks, jaw, chin, mouth, nose, ears) from the elements associated with outdoor activities such as, but not limited to, during boat travel in sport leisure and commercial fishing, snowboarding, skiing, snowmobiling, hiking, hunting, paint ball, law enforcement, fire fighting, motorcycling, dune buggy or rails, ATV, air soft, spectator sports (e.g., NASCAR car racing, NFL/college football, NHL/college hockey), commercial activities such as airline industry, landscaping, and governmental activities such as military, lake patrols, etc.

The face protector 700 includes a face plate 710 preferably made of an injection molded thin, plastic material. The face plate 710 has a configuration generally similar to the configuration of a human face and includes a forehead portion 720, a cheek portion 730, a jaw portion 740, a mouth portion 742, a nose portion 744, ear portions 746, a chin portion 748, and a replaceable/interchangeable transparent, plastic visor/lens 750 that cover and protect the forehead, cheeks, jaw, mouth, nose, ears, chin, and eyes, respectively, of a user.

The forehead portion 720 is just wider than the width of the head of the user, is curved rearwardly, and extends from the brow area to just above the forehead area of the user. Substantially all of the skull is not covered by the forehead portion 720 or the rest of the face protector 700. Although not shown, in alternative embodiments, the forehead portion 720 may include one or more ventilation sections for ventilating the face protector 700. On a front side 760 of the forehead portion 720, the forehead portion 720 includes an oval section insert 782 that fits within a corresponding oval recess. The oval section insert 782 preferably includes a trademark, logo, or other insignia pertinent to the application of the face protector 700. For example, for a fishing application, the oval section insert 782 may include one type of logo/trademark, for a motorcycle application, the oval section insert 782 may include a different type of logo/trademark, for a paintball application, the oval section insert 782 may include a different type of logo/trademark, and for a snowboarding/skiing application, the oval section insert 782 may include a different type of logo/trademark. Alternatively, the mold used to make the face protector 700 may include different mold inserts for the different logos so that the same mold, but different mold inserts, may be used to manufacture the face protectors for different applications.

The cheek portion 730 is curved rearwardly from the nose portion 744 and the mouth portion 742 of the face plate 710, and protects the cheeks of a user from the environment.

The jaw portion 740 is curved rearwardly from the mouth portion 742 and the cheek portion 730 of the face plate 710, and protects the jaw area of a user. The jaw portion 740 includes the chin portion 748, which has a cupped configuration for receiving the chin of a user. The jaw portion 740 decreasingly tapers in width from the top of the jaw portion 740, just below the lens 750, to the bottom of the chin portion 748.

The mouth portion 742 is disposed between the nose portion 744 and the jaw portion 740, and protects the mouth of a user. Although not shown, in an alternative embodiment, the mouth portion 742 may include ventilation holes in the grooves shown or in other areas of the mouth portion 742 and/or nose portion 744. For example, for a fishing application, the mouth portion 742 may not include ventilation holes because during boating the high relative speed of the air compared to the face protector 700 removes the user's exhaled breath of air, preventing the lens 750 from becoming fogged up. For other applications, such as a snowboarding/skiing application, the mouth portion 742 may include ventilation holes. The mold used to make the face protector 700 may include different inserts for the different mouth and/or nose designs so that the same mold, but different inserts, may be used to manufacture the face protectors for different applications (e.g. face protectors with and without mouth/nose ventilation holes).

The front side 760 of the nose portion 744 may bow outward and the rear side 762 of the nose portion 744 may be concave to accommodate the nose of the user. Although not shown, as discussed above, the nose portion 744 may include one or more ventilation holes in alternative embodiments.

The ear portions 746 extend rearwardly from the opposite ends of the lens 750, and decreasingly taper in dimension progressing rearwardly, and protect the entire ears of the user. On the front side 760 of the ear portions 746, over the areas where the user's ears would be located, snap connections 752 are disposed.

Figure 3:
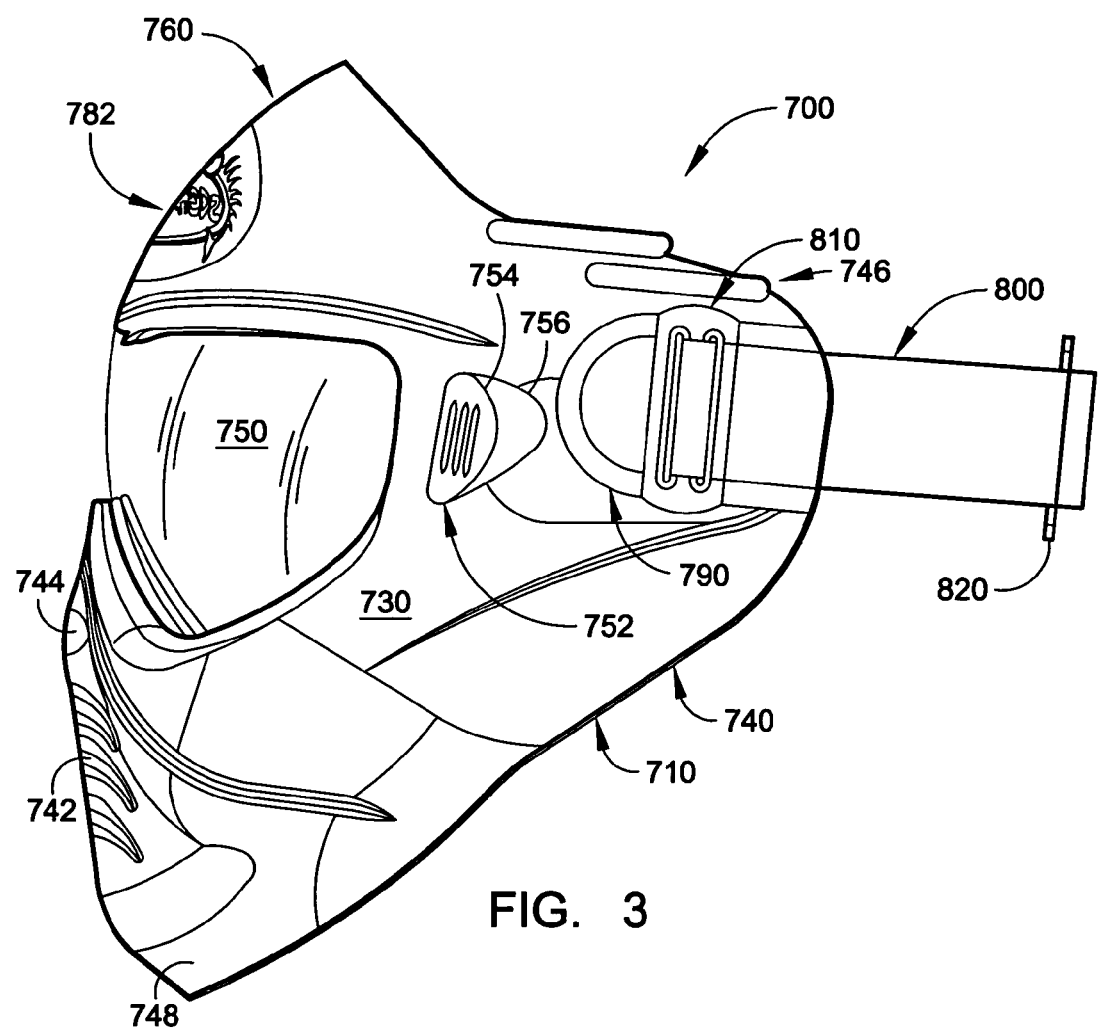
FIG. 3 is a right side-elevational view of the face protector illustrated in FIG. 1, the left side-elevational view being a mirror image thereof.
Figure 5:
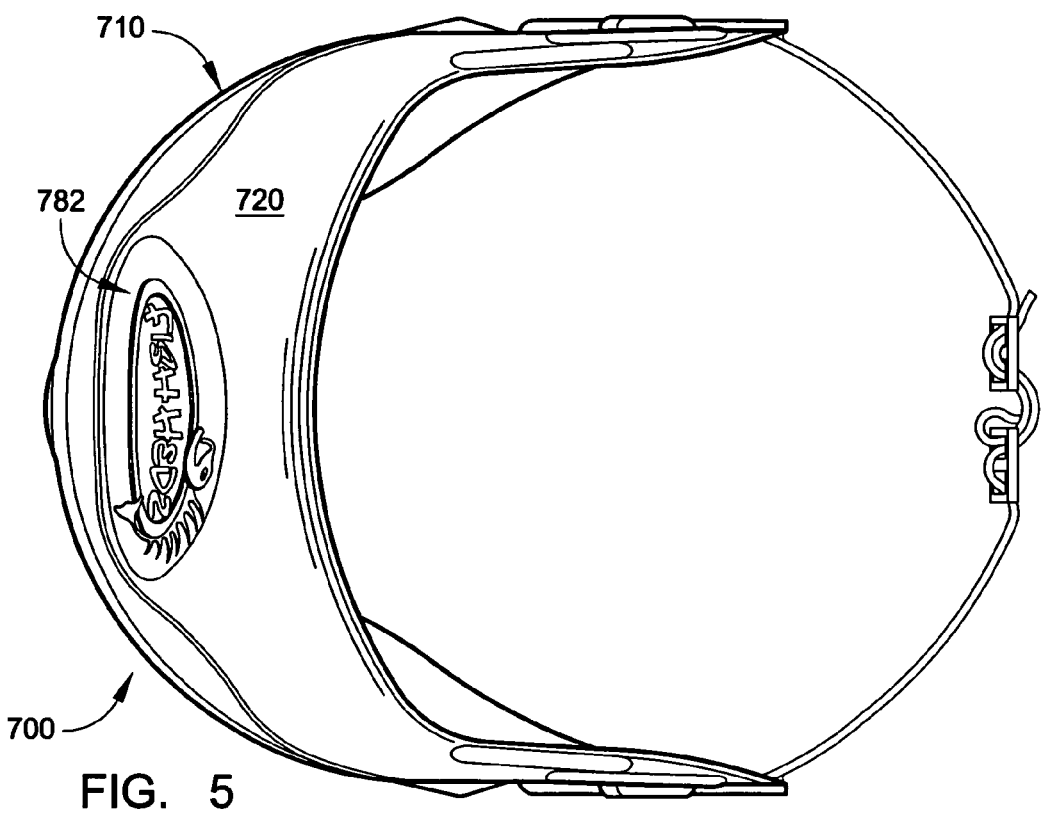
FIG. 5 is a top plan view of the face plate protector illustrated in FIG. 1.
Figure 6:
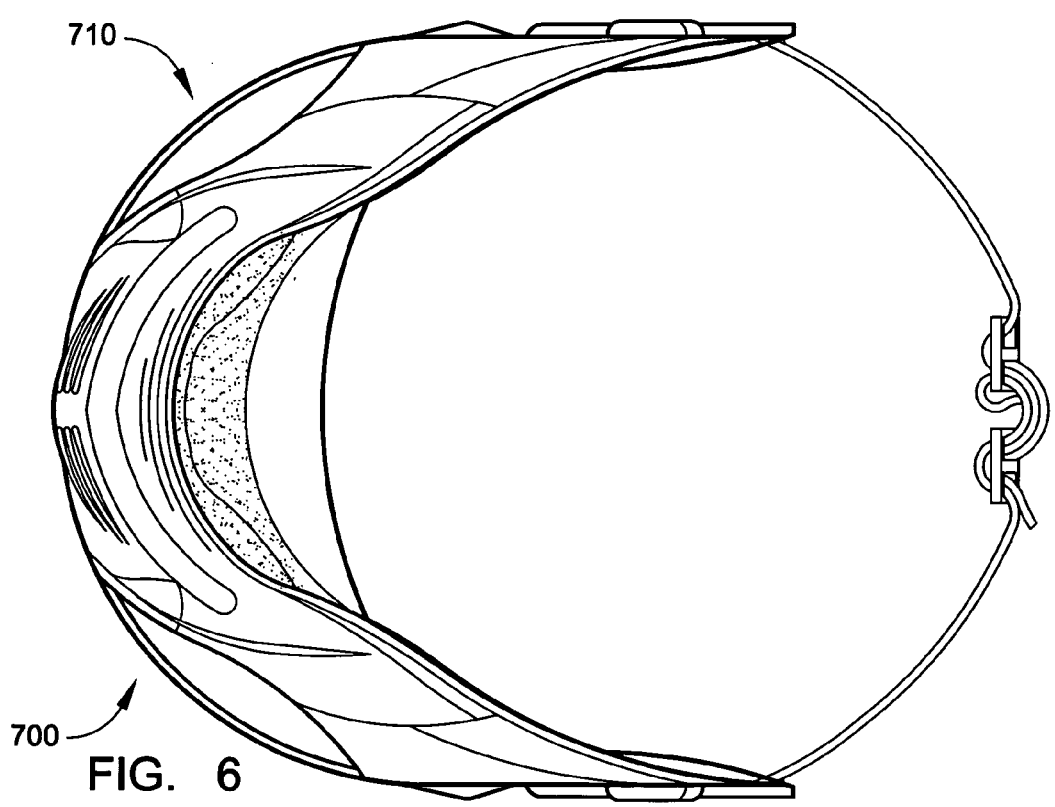
FIG. 6 is a bottom plan view of the face plate protector illustrated in FIG. 1.

The transparent lens 750 protects the user's eyes from the environment, and maximizes the user's peripheral vision while eliminating eye strain and eye fatigue. The lens 750 fits within a front opening in the eye portion of the face plate 710 and connects to the face plate 710 at snap connection 752. Ends of the lens 750 include protruding snap members 754 that snap into recesses 756 below the temple portions of the face plate 710. The snap members 754 and recesses 756 form the snap connections 752. As illustrated in FIG. 3, the lens 750 is substantially flush with the front side 760 of the forehead portion 720 which is configured to protect the forehead.

Figure 7:
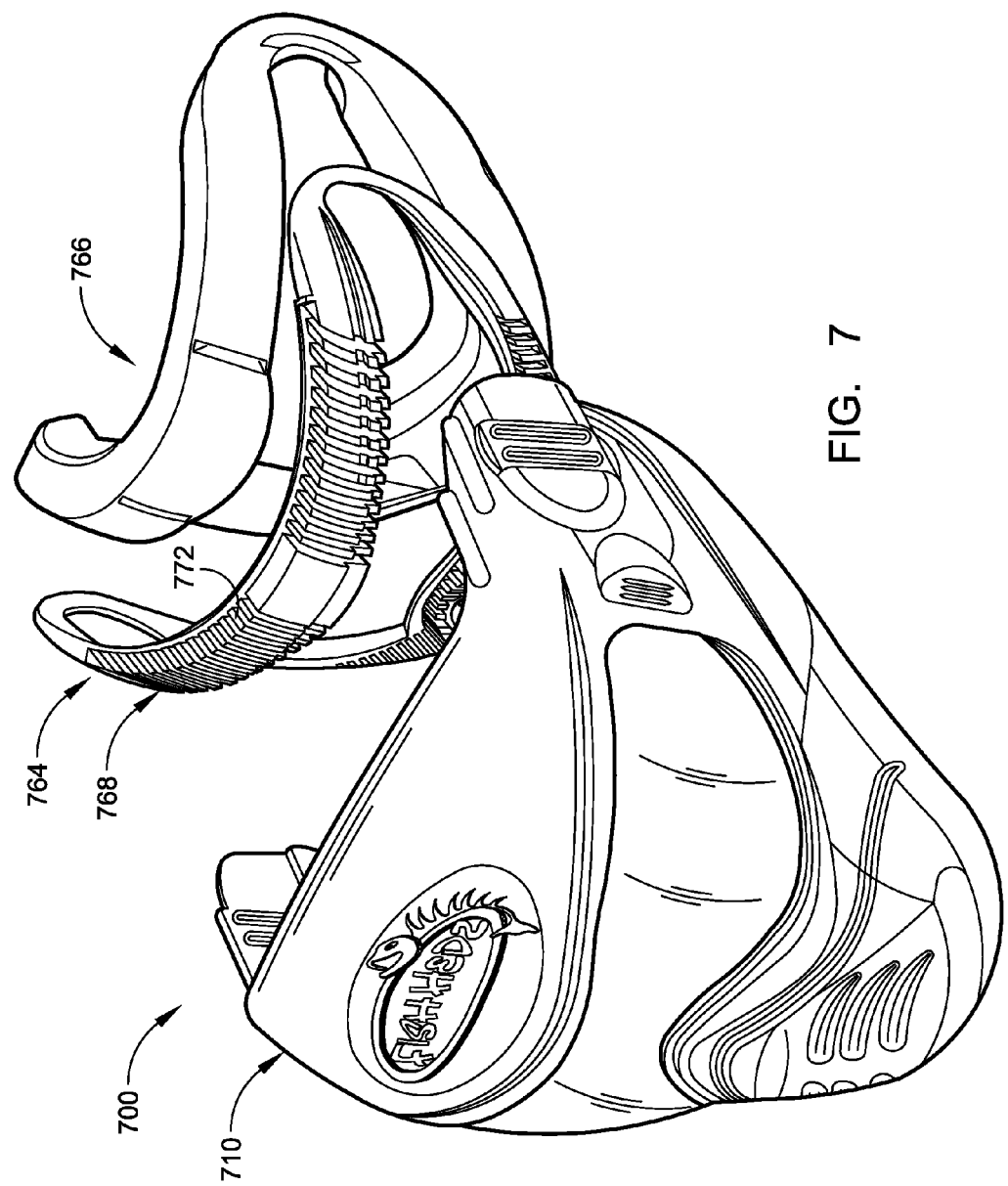
FIG. 7 is an exploded front perspective view of the face protector illustrated in FIG. 1.
Figure 8:
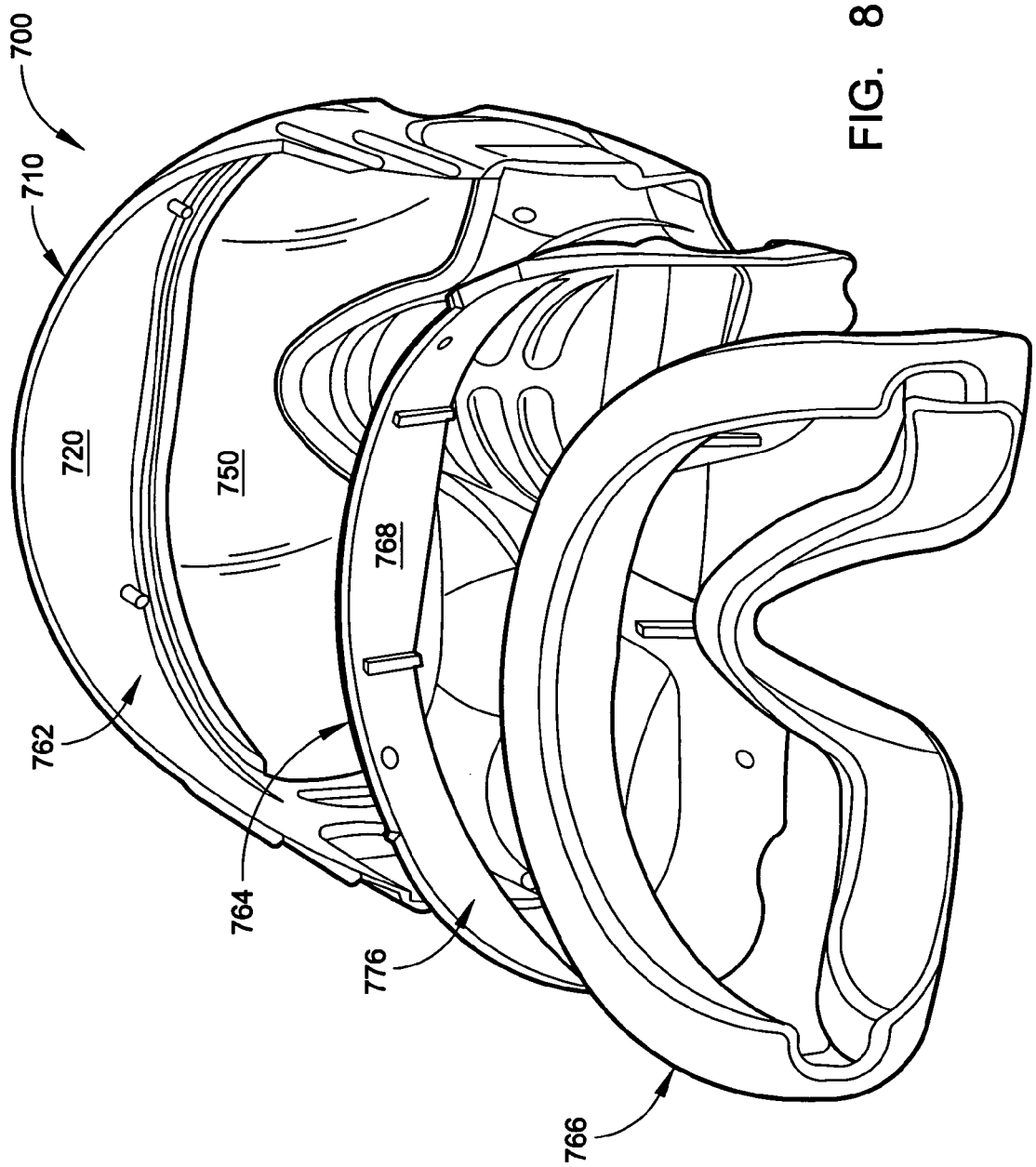
FIG. 8 is an exploded rear perspective view of the face protector illustrated in FIG. 1.
Figure 9:
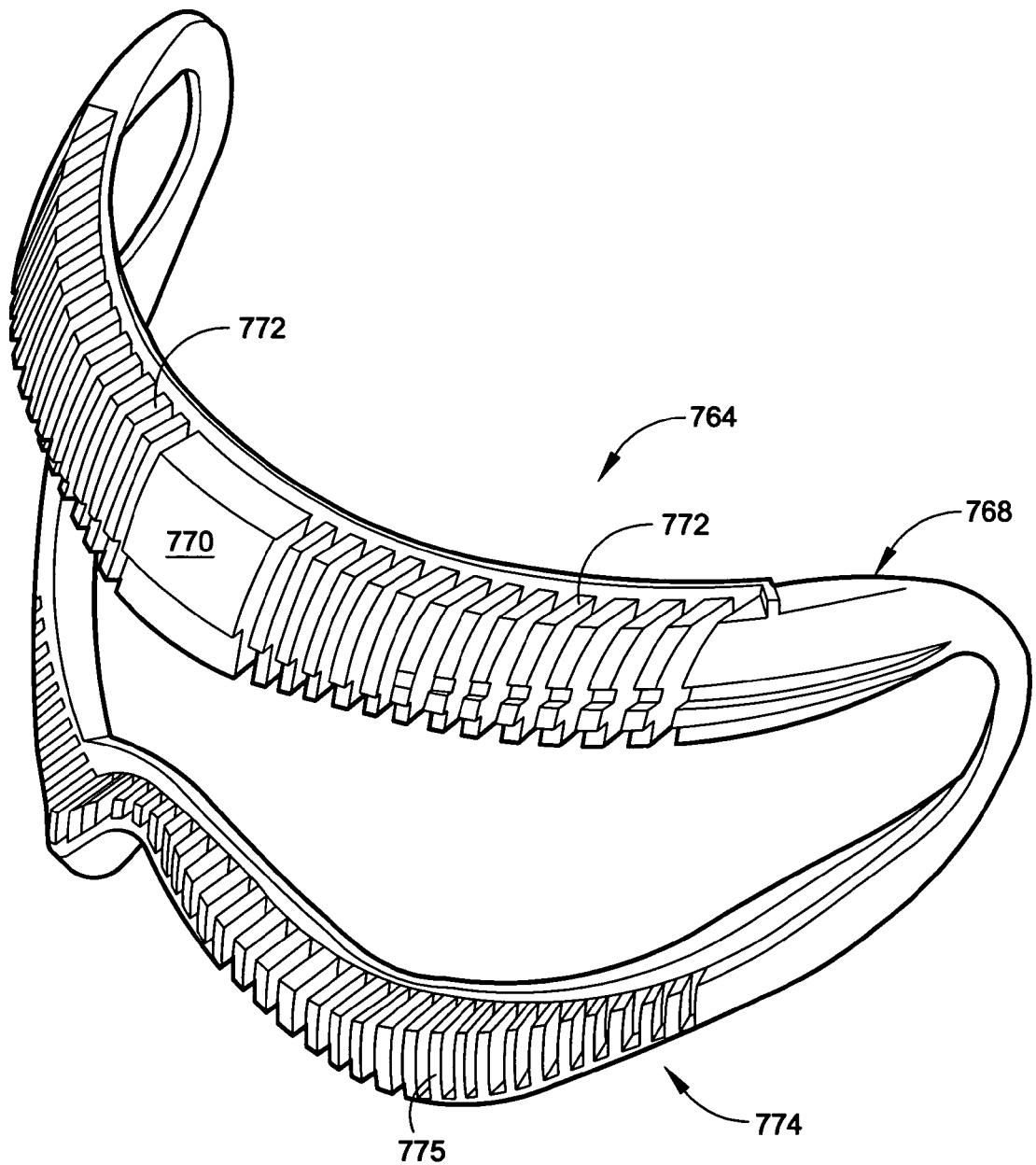
FIG. 9 is a perspective view of an embodiment of an insert for the face protector illustrated in FIG. 1.

With reference in particular to FIGS. 7–9, a plastic ski goggle-shaped insert 764 is disposed between the rear side 762 of the face plate 710 and a ski goggle-shaped cushion member 766. The insert 764 has a one-piece continuous and integrated configuration. A front part of forehead portion 768 includes a centrally disposed smooth glue surface 770 for adhering the insert 764 to the rear side 762 of the forehead portion 720. Disposed laterally of the glue surface 770 on the forehead portion 768 are vertical ventilation tracks 772. The ventilation tracks 772 provide ventilation to the rear side 762 of the lens 750. A cheek portion 774 of the insert 764 includes molded vertical ribs 775. An adhesive and/or fasteners may be used to fasten the insert 764 to the face plate 710.

The cushion member 766 has a ski goggle-shaped configuration similar to the configuration of the insert 764, and is fastened to a rear side 776 of the insert 764 using an adhesive and/or fasteners. The cushion member 766 is made of a waterproof, breathable material, and provides added comfort to the user when wearing the face protector 700. The cushion member 766 may include holes therein to increase the breathability and comfort of the cushion member(s) when against the skin of the user. The cushion member(s), like the face plate 710 and the insert 764, may come in different sizes to allow the user to custom fit the face protector 700 for the user's specific facial dimensions.

With reference back to FIGS. 3 and 4, a waterproof and/or water-resistant elastic, adjustable strap 800 is used to retain the face protector 700 in position on the user's head. Opposite ends of the strap 800 include strap connectors 810 that snap into respective snap receiving sections 790 for connecting the strap 800 to the face protector 700. The strap 800 includes adjustment slides 820 for adjusting the length of the strap 800.

Although not shown, in an alternative embodiment, in addition to or instead of the strap 800, the face protector 700 may be donned to the user's head using a detachable waterproof and/or water-resistant elastic hood. The hood is worn over the back portion of a user's head to help support the face plate 710 and protect the upper and rear areas of a user's head from the environment. The hood is preferably made of a waterproof, breathable, windproof, durable fabric such as, but not limited to, GORE-TEX® sold by the W.L. Gore & Associates, Inc. of Newark, Del. Another material that may be used is sold under the trademark NOMEX® by E.I. du Pont de Nemours and Company of Wilmington, Del. One or more tightening straps may be incorporated in the hood to tighten the hood to the user's head.

The face protector 700 may come in a one-size-fits-all configuration or may come in different sizes for different-sized heads (e.g., an adult size, a child size).

Figure 10:
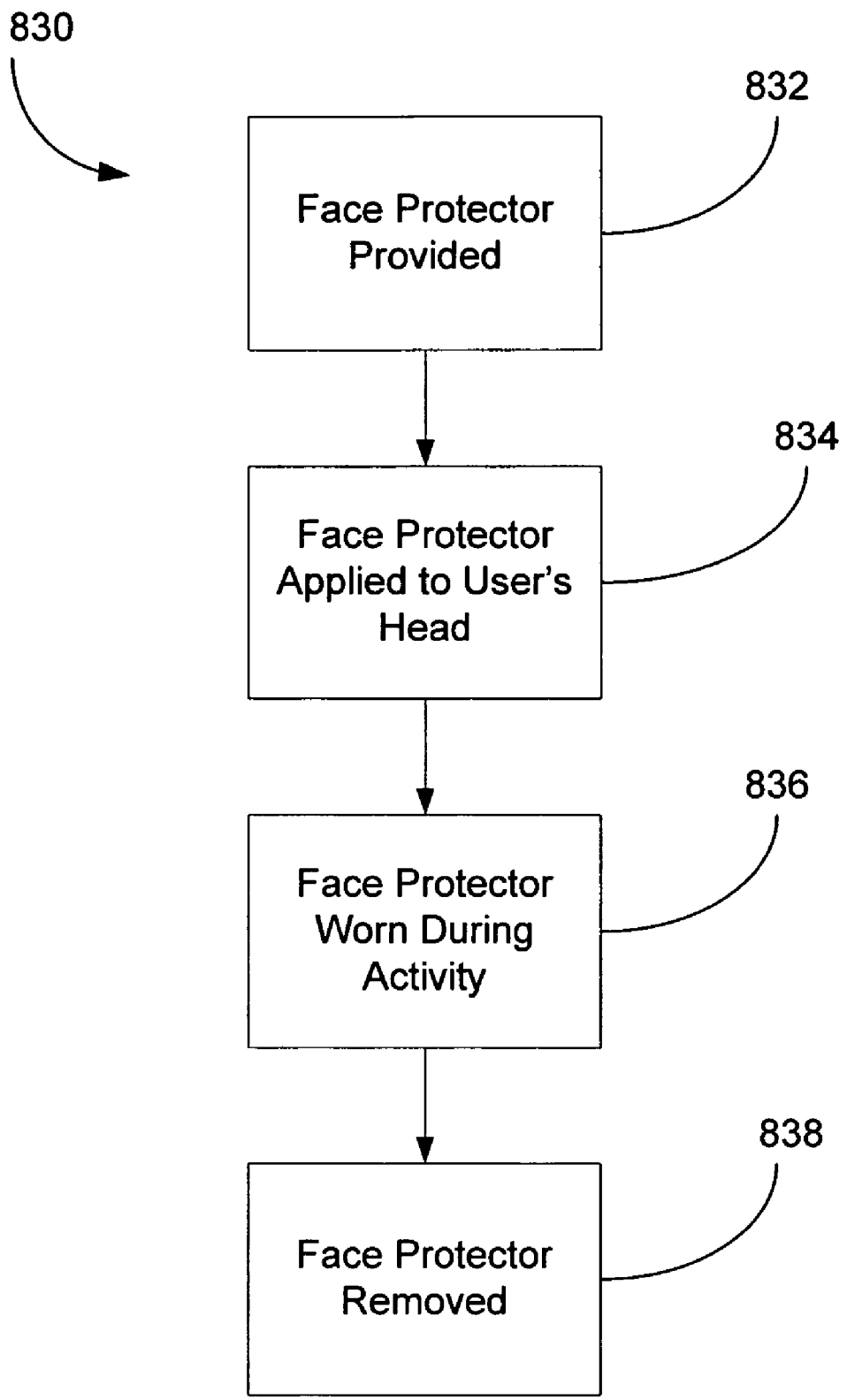
FIG. 10 is a flow chart of an exemplary method of using the face protector.

With reference to FIG. 10, an exemplary method 830 of using the face protector 700 to protect one's face from the outdoor elements in a fishing/boating application will described. As will be described in more detail, the enumerated generic steps 832–838 of the method 830 apply to a number of different applications and are incorporated therein, which are set forth below.

For example, but not by way of limitation, in the exemplary application of the face protector 700 where the face protector 700 is donned by a fisherman or boater exposed to the environment on an open boat before boating to a fishing location or other location, at step 832, the face protector 700 is provided. At step 834, the face protector is applied to the user's head. The face protector 700 is put on by sliding the face protector 700 and strap 800 over the user's head so that the face protector 700 is over the user's face and the strap 800 is behind the user's head. The face plate 710 may be tightened to the user's head by reducing the length of the strap 800 with the adjustment slides 820. At step 836, the face protector 700 is worn on the face during the activity. In the boating/fishing example, during transport, the face protector 700 allows the fisherman or boater to be exposed to all types of conditions while protecting one's face (e.g., from insects, rain, water spray, sleet, snow, branches, leaves, etc.). If the weather is inclement, the face protector 700 may be worn while fishing (or when the boat is stopped) to protect the user's face from wind, rain, sleet or other inclement weather. At step 838, the face protector is removed from the user's head after the activity. The face protector 700 is removed by sliding the face protector 700 and strap 800 off of the user's head, and removing the face protector 700 and strap 800 from the user's head.

The strap 800 and the face plate 710 are attached and detached by snapping the snap connectors 810 into the snap receiving sections 790 and unsnapping the snap connectors 810 with respect to the snap receiving sections 790. The strap 800 may be detached from the face plate 710 for cleaning the strap 800 and/or face plate 710. Likewise, the lens 750 may be added to or removed from the face plate 710 using the snap connections 752 for cleaning the lens 750, replacing the lens 750, and/or interchanging lenses 750.

The enumerated generic steps 832–838 of the method 830 apply to each of the following applications and are incorporated therein: The face protector 700 may be worn by a user during snowboarding/skiing to protect one's face; the face protector 700 may be worn by a user during dune buggy riding to protect one's face; the face protector 700 may be worn by a user during snowmobiling to protect one's face; the face protector 700 may be worn by a user during hiking to protect one's face; the face protector 700 may be worn by a user during hunting to protect one's face; the face protector 700 may be worn by a user during air soft playing (like paintball, but small plastic BBs used instead of paint balls) to protect one's face; the face protector 700 may be worn by a user during paint ball play to protect one's face; the face protector 700 may be worn by a user during law enforcement activity to protect one's face; the face protector 700 may be worn by a user during fire fighting to protect one's face; the face protector 700 may be worn by a user during motorcycling to protect one's face; the face protector 700 may be worn by a user during ATV riding to protect one's face; the face protector 700 may be worn by a user during commercial activities (e.g., airline industry, landscaping) to protect one's face; the face protector 700 may be worn by a user during governmental activities (e.g., military, lake patrols) to protect one's face; and the face protector 700 may be worn by a user while watching spectator sports (e.g., NASCAR car racing, NFL/college football, NHL/college hockey) to protect one's face.

The face protector 700 not only protects the forehead, face, eyes, cheeks, jaw, chin, mouth, ears, and nose from the elements associated with an outdoor activity or activity, but also is small, light-weight, stowable, comfortable, compactable, durable, and water-resistant/waterproof. In the exemplary fishing/boating application described above, the small, light-weight, stowable, comfortable, compactable, durable, and water-resistant/waterproof aspects of the face protector 700 make it idea for use and storage on a boat.

Figure 11:
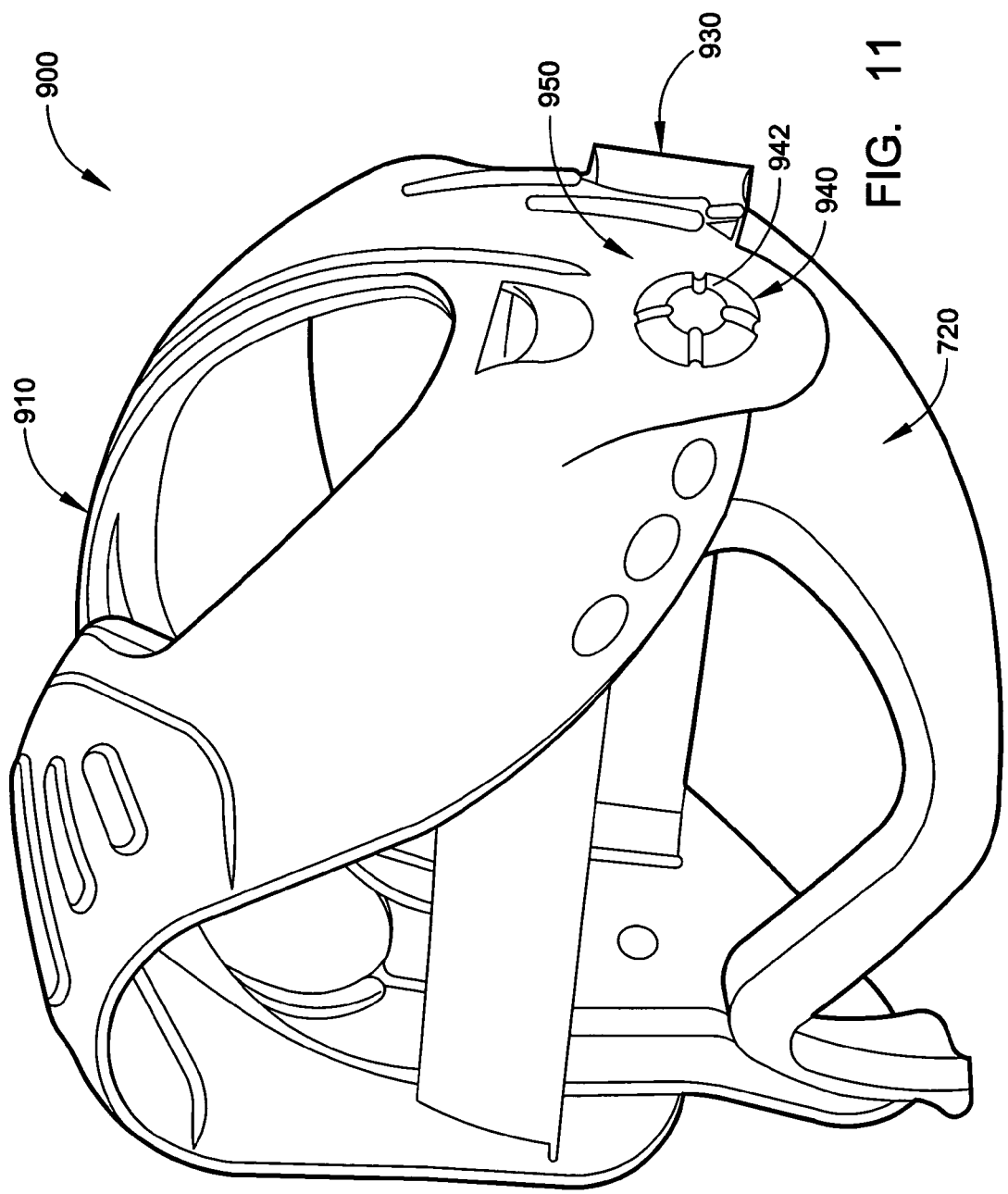
FIG. 11 is a front perspective view of another embodiment of a face protector with a face plate shown in a retracted position relative to a goggle frame.

With reference to FIG. 11, another embodiment of a face protector 900 will be described. The face protector 900 includes a face plate 910 that is substantially the same as face plate 710 described above with respect to FIGS. 1–6, and, therefore, will not be described in further detail. The face protector 900 includes a stationary goggle frame 920 that is connected to the user's head with a strap 930 similar to strap 800 described above (the frame 920 and strap 930 include snap receiving sections and strap connectors similar to snap receiving sections 790 and strap connectors 810 described above). The face plate 910 is pivotally connected to the frame 920 at opposite pivot points 940 (through pivot member 942) in the ear portions 950 of the face protector 900 and frame 920. The stationary goggle frame 920 is similar in configuration to (and is worn in a similar manner as) a pair of ski goggles. The frame 920 includes one or more breathable cushion members on a rear side of the frame 920 for user comfort. The face protector 900 is used in a similar manner and for similar applications to those described above with respect to face protector 700, except the face plate 910 may be retracted relative to the stationary goggle frame 920 during use.

To retract the face plate 910, the user grabs the face plate 910 and pivots the face plate upwardly relative to the stationary goggle frame 920, into the position shown in FIG. 11. In this position, the face plate 910 is no longer in front of the user's face. When the user desires face protection, the face plate 910 is pivoted downward, to a deployed position in front of the user's face. In an alternative embodiment, the face plate 910 may be used with a hood in addition to or instead of the stationary goggle frame 920.

Figure 12:
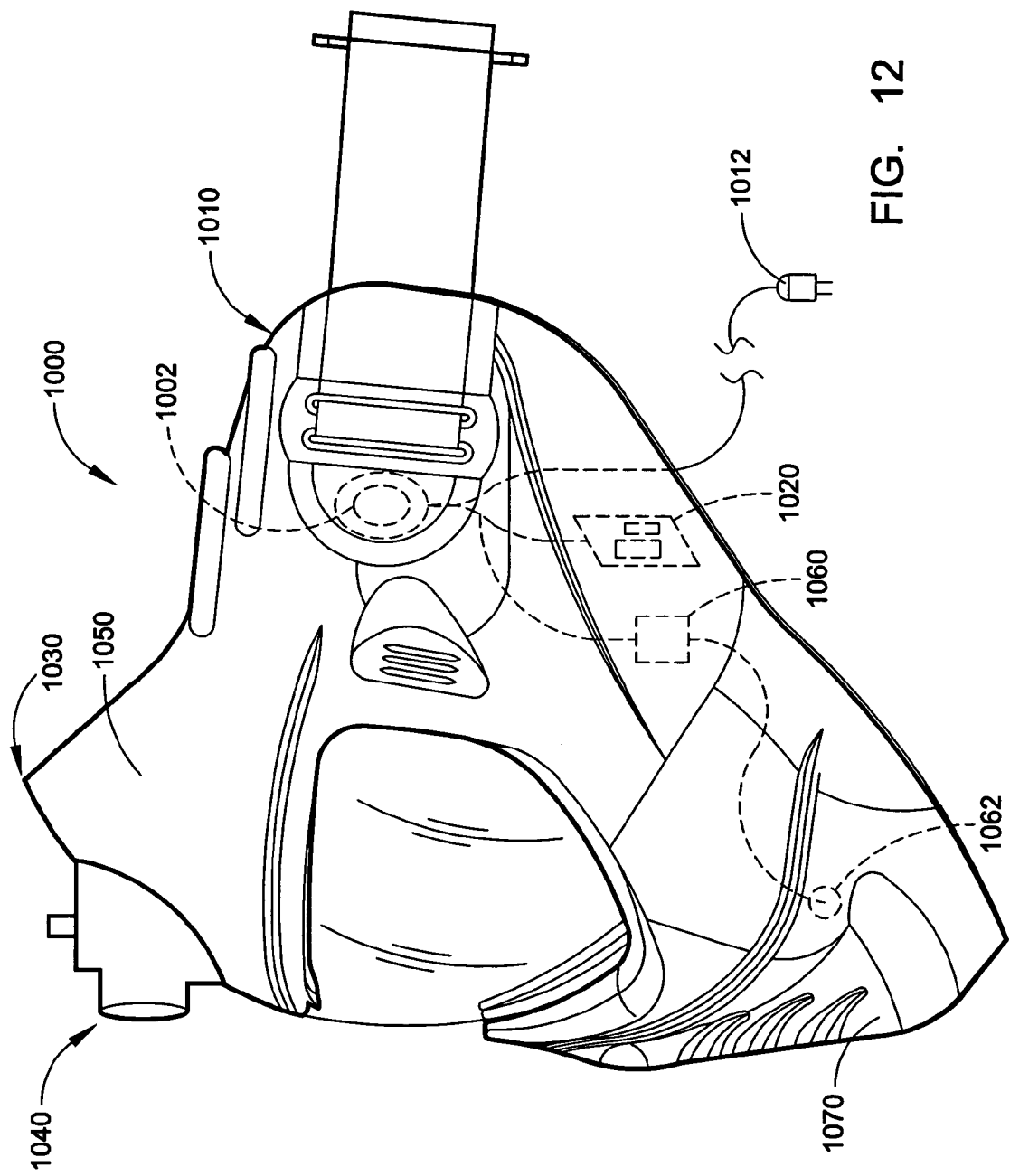
FIG. 12 is a right side-elevational view of a further embodiment of a face protector.

With reference to FIG. 12, a further embodiment of a face protector 1000 will now be described. The face protector 1000 is the same as face protector 700 described above with respect to FIGS. 1–9, except the face protector 1000 includes opposite headphone speakers 1002 in ear portions 1010 with wire/plug 1012 (for plugging into a separate CD player, MP3 player, Apple IPOD (or other musical device with hard drive), AM and/or FM receiver/tuner, two-way radio, etc.), AM and/or FM receiver/tuner 1020 in face plate 1030, flashlight 1040 in the forehead portion 1050, and two-way radio 1060 in the face plate 1030 with attached microphone 1062 in mouth portion 1070.

In further embodiments of the face protector, one or more of these elements may be included in the face protector 700/1000.

In still further embodiments, one or more of these elements may be included in the face protector 900.

The face protector with one or more of these elements is used in a similar manner and for similar applications to those described above with respect to face protector 700, except a user may listen to a separate CD player, MP3 player, Apple IPOD (or other musical device with hard drive), AM and/or FM receiver/tuner, two-way radio, etc. using the headphone speakers 1002 and wire/plug 1012; a user may listen to the integrated AM and/or FM receiver/tuner 1020 using the headphone speakers 1002; a user may use the flashlight 1040 to illuminate objects in the dark; and/or may communicate with others wearing a similar type of face protector using the two-way radio 1060 and microphone 1062. In spectator sport applications with the face protector, the spectator may, for example, but not by way of limitation, tune into his or her favorite pit crew with the AM and/or FM receiver/tuner 1020 when watching a live NASCAR (or other car racing event), or may tune into the radio station covering the sports event with the AM and/or FM receiver/tuner 1020 when watching the live sports event.

While the particular devices and methods herein shown and described in detail are fully capable of attaining the above described objects of this invention, it is to be understood that the description and drawings presented herein represent presently preferred embodiments of the invention and are therefore representative of the subject matter which is broadly contemplated by the present invention. It is further understood that the scope of the present invention fully encompasses other embodiments that may become obvious to those skilled in the art having the benefit of this disclosure and that the scope of the present invention is accordingly limited by nothing other than the appended claims.

What is claimed is:

1. A method of using a face protector, comprising:
   providing a face protector including a single-piece face plate with integral portions configured to protect the forehead, cheeks, jaw, chin, mouth, ears, and nose of a user without protecting substantially the remainder of the user's head, a lens directly connected to the face plate and substantially flush with the portion configured to protect the forehead, and a strap directly connected to the portion configured to protect the ears;
   applying the face protector to the user's head;
   wearing the face protector during an activity;
   removing the face protector after the activity.

2. The method of claim 1, wherein applying includes applying the face protector to the user's head by sliding the face plate and strap over the users head and securing the face plate in position in front of the user's face with the strap.

3. The method of claim 1, wherein providing includes providing the face protector with a goggle-shaped cushion member and a goggle-shaped insert disposed between the goggle-shaped cushion member and the face plate.

4. The method of claim 3, wherein the goggled-shaped insert includes means for ventilating the face protector.

5. The method of claim 1, wherein the activity is one of fishing and boating, and wearing includes wearing the face protector during one of fishing and boating to protect the user's face.

6. The method of claim 1, wherein the activity is one of skiing and snowboarding, and wearing includes wearing the face protector during one of skiing and snowboarding to protect the user's face.

7. The method of claim 1, wherein the activity is snowmobiling, and wearing includes wearing the face protector during snowmobiling to protect the user's face.

8. The method of claim 1, wherein the activity is one of ATV riding and dune buggy riding, and wearing includes wearing the face protector during one of ATV riding and dune buggy riding to protect the user's face.

9. The method of claim 1, wherein the activity is one of hiking and hunting, and wearing includes wearing the face protector during one of hiking and hunting to protect the user's face.

10. The method of claim 1, wherein the activity is one of a commercial activity, an aviation-related activity, and landscaping, and wearing includes wearing the face protector during one of the commercial activity, the aviation-related activity, and landscaping to protect the user's face.

11. The method of claim 1, wherein the activity is one of paint ball playing and air soft playing, and wearing includes wearing the face protector during one of paint ball playing and air soft playing to protect the user's face.

12. The method of claim 1, wherein the activity is one of a governmental activity and a military activity, and wearing includes wearing the face protector during one of the governmental activity and the military activity to protect the user's face.

13. The method of claim 1, wherein the activity is one of law enforcement and fire fighting, and wearing includes wearing the face protector during one of law enforcement and fire fighting to protect the user's face.

14. The method of claim 1, wherein the activity is sports watching, and wearing includes wearing the face protector during sports watching to protect the user's face.

15. The method of claim 3, wherein the goggled-shaped insert includes a one-piece continuous and integrated configuration.

16. The method of claim 3, wherein the goggled-shaped insert includes a centrally disposed smooth surface for adhering the insert to a rear side of the face plate.

17. The method of claim 3, wherein the goggled-shaped insert includes vertical ventilation tracks to provide ventilation to a rear side of the lens.

18. The method of claim 3, wherein the goggled-shaped insert includes a cheek portion with vertical ribs.

* * * * *